US010883963B2

(12) United States Patent
Mizumura et al.

(10) Patent No.: US 10,883,963 B2
(45) Date of Patent: Jan. 5, 2021

(54) ELECTROCHEMICAL MEASUREMENT USING PHENYLENEDIAMINE DERIVATIVE

(71) Applicants: SEIKAGAKU CORPORATION, Tokyo (JP); TOHOKU UNIVERSITY, Sendai (JP)

(72) Inventors: Hikaru Mizumura, Tokyo (JP); Toshio Oda, Tokyo (JP); Tomokazu Matsue, Sendai (JP); Kumi Inoue, Sendai (JP)

(73) Assignees: SEIKAGAKU CORPORATION, Tokyo (JP); TOHOKU UNIVERSITY, Sendai (JP)

( * ) Notice: Subject to any disclaimer, the term of this patent is extended or adjusted under 35 U.S.C. 154(b) by 129 days.

(21) Appl. No.: 16/076,614

(22) PCT Filed: Feb. 15, 2017

(86) PCT No.: PCT/JP2017/005514
§ 371 (c)(1),
(2) Date: Aug. 8, 2018

(87) PCT Pub. No.: WO2017/141961
PCT Pub. Date: Aug. 24, 2017

(65) Prior Publication Data
US 2019/0049408 A1 Feb. 14, 2019

(30) Foreign Application Priority Data
Feb. 16, 2016 (JP) .................. 2016-026925

(51) Int. Cl.
| G01N 27/48 | (2006.01) |
| C07C 211/51 | (2006.01) |
| G01N 33/579 | (2006.01) |
| C07K 9/00 | (2006.01) |
| G01N 33/487 | (2006.01) |
| C07K 14/195 | (2006.01) |
| G01N 27/447 | (2006.01) |

(52) U.S. Cl.
CPC ............ *G01N 27/48* (2013.01); *C07C 211/51* (2013.01); *C07K 9/00* (2013.01); *C07K 14/195* (2013.01); *G01N 27/44726* (2013.01); *G01N 33/487* (2013.01); *G01N 33/579* (2013.01); *G01N 2400/24* (2013.01); *G01N 2400/50* (2013.01); *Y02P 20/55* (2015.11)

(58) Field of Classification Search
CPC .. C07C 211/51; G01N 27/48; G01N 2400/24; G01N 2400/50; G01N 27/44726; G01N 33/487; G01N 33/579; G01N 27/416; C07K 14/195; C07K 9/00; Y02P 20/55
See application file for complete search history.

(56) References Cited

U.S. PATENT DOCUMENTS

| 4,681,841 A | 7/1987 | Matsumoto et al. |
| 6,495,336 B1 | 12/2002 | Ludin et al. |
| 2003/0146113 A1 | 8/2003 | Unkrig et al. |

FOREIGN PATENT DOCUMENTS

| CN | 102305788 A | 1/2012 |
| DE | 3342109 A | 5/1985 |
| EP | 0663446 A2 | 7/1995 |
| JP | S56-042597 A | 4/1981 |
| JP | 2002-542154 A | 12/2002 |
| JP | 2003-524184 A | 8/2003 |
| JP | 2015-187607 A | 10/2015 |

OTHER PUBLICATIONS

The STN Registry File for RN 623-09-6 disclosed in 1984 downloaded from STN on Mar. 31, 2020 (Year: 1984).*
The STN Registry File for RN 99-98-9 disclosed in 1984 downloaded from STN on Mar. 31, 2020 (Year: 1984).*
Babich et al. Toxicol. Letters (1992) 63: 171-179 (Year: 1992).*
Database Caplus, Chemical Abstract (STN) Accession No. 2002:394170 (2002) [abstract of Wei et al., "Application of four electrochemical substrates of horseradish peroxidase-based voltammetric enzyme immunoassay for the detection of tobacco mosaic virus," *Journal of Qingdao Institute of Chemical Technology*, 23(1): 1-3 (2002)].
Database WPI, Derwent World Patents Index Accession No. 1981-41227D (1981) [abstract of JP S56-042597].
Database WPI, Derwent World Patents Index Accession No. 2012-B14655 (2012) [abstract of CN 102305788].
Wei et al., "Application of four electrochemical substrates of horseradish peroxidase-based voltammetric enzyme immunoassay for the detection of tobacco mosaic virus," *Journal of Qingdao Institute of Chemical Technology*, 23(1): 1-3 (2002).

(Continued)

*Primary Examiner* — Susan M Hanley
(74) *Attorney, Agent, or Firm* — Leydig, Voit & Mayer, Ltd.

(57) ABSTRACT

The present invention addresses the problem of providing a means for making highly sensitive and stable measurements possible using electrochemical measurement methods. This problem is resolved by providing: a labeling substance represented by general formula (1) and used to label a substrate; a measurement substrate that is formed by being labeled using the labeling substance; a method of measuring using electrochemical measurement methods that use the measurement substrate; and a reagent kit that includes as components the labeling substance and/or the measurement substrate.

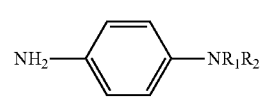

(1)

(In general formula (1), $R_1$ is either H or an alkyl group ($C_mH_{2m+1}$), m is an integer of 1-4, $R_2$ is an alkyl group ($C_nH_{2n+1}$), and n is an integer of 1-4.)

5 Claims, No Drawings

Specification includes a Sequence Listing.

(56) References Cited

OTHER PUBLICATIONS

European Patent Office, Extended European Search Report in European Patent Application No. 17753217.3 (dated Sep. 30, 2019).
Japanese Patent Office, International Search Report in International Patent Application No. PCT/JP2017/00514 (dated May 23, 2017).
Japanese Patent Office, Notice of Reasons for Refusal in Japanese Patent Application No. 2018-500152 (dated Sep. 8, 2020).

* cited by examiner

ELECTROCHEMICAL MEASUREMENT USING PHENYLENEDIAMINE DERIVATIVE

CROSS-REFERENCE TO RELATED APPLICATIONS

This patent application is the U.S. national phase of International Patent Application No. PCT/JP2017/005514, filed Feb. 15, 2017, which claims the benefit of Japanese Patent Application No. 2016-026925, filed on Feb. 16, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 470 bytes ASCII (Text) file named "739807SequenceListing.txt," created Aug. 8, 2018.

TECHNICAL FIELD

The present invention relates to a means for a highly sensitive and stable measurement using an electrochemical measurement method, and specifically, to a labeling substance to label a substrate, a substrate for measurement labeled by the labeling substance, a measurement method by an electrochemical measurement method using the substrate for measurement, and a reagent kit including, as components, the labeling substance and/or the substrate for measurement.

BACKGROUND ART

In hygiene management of pharmaceuticals and foods and the diagnosis of animals including humans, a means to sense microbially derived substances and measure the level of microbial contamination is important. As a means to measure a level of microbial contamination, a Limulus test is in widespread use. The Limulus test is a technique to measure the level of microbial contamination by using endotoxin or (1→3)-β-D-glucan as a measurement target substance, and is a measurement method using the properties of protease precursors from horseshoe crab those are activated by these measurement target substances. Although the Limulus test has been generally performed by a gelation method, turbidimetric method, or colorimetric method, a Limulus test using an electrochemical measurement method has also been developed in recent years.

Patent Literature 1 discloses that, in a Limulus test using an electrochemical measurement method, a para-aminophenol derivative such as para-methoxyaniline contributes to highly sensitive and stable detection of endotoxin.

Patent Literature 2 discloses an oligopeptide derivative to be used in a measurement of protease activity by an electrochemical measurement method. An aniline derivative is bonded to the C-terminus of this peptide derivative.

However, none of the literatures listed above discloses that a phenylenediamine derivative is usable in an electrochemical measurement. These literatures also include no suggestion that a phenylenediamine derivative is a compound that enables a higher sensitive and more stable measurement of protease activity than compounds conventionally used.

CITATION LIST

Patent Literatures

Patent Literature 1: Japanese Published Unexamined Patent Application No. 2015-187607
Patent Literature 2: Japanese Translation of International Application (Kohyo) No. 2002-542154

SUMMARY OF THE INVENTION

Technical Problem

An object of the present invention is to provide a means to enable a highly sensitive and stable measurement in a measurement using an electrochemical measurement method.

Solution to Problem

As a result of intensive research and study to solve the above-described problem, the inventors of the present invention found that by labeling a substrate with N-methyl-p-phenylenediamine (MPDD) or N, N-dimethyl-p-phenylenediamine (DMPD), the substrate could be used as a substrate for measurement suitable for a measurement using an electrochemical measurement method, and accordingly, a highly sensitive and stable electrochemical measurement method can be performed, thus completing the present invention.

The problem described above can be solved by the present invention including the following mode.

[1]
A labeling substance containing a structure represented by the following general formula (1), and to be used to label the substrate to obtain a substrate for measurement suitable for a measurement using an electrochemical measurement method.

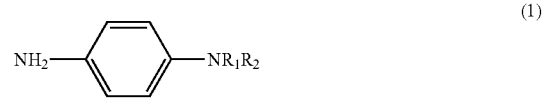

(1)

(In formula (1) above, $R_1$ is H or an alkyl group ($C_mH_{2m+1}$), m is an integer of 1 to 4, $R_2$ is an alkyl group ($C_nH_{2n+1}$), and n is an integer of 1 to 4.)

[2]
The labeling substance according to [1], wherein $R_1$ is H or a methyl group ($CH_3$), and $R_2$ is a methyl group ($CH_3$).

[3]
A substrate for measurement suitable for a measurement using an electrochemical measurement method, containing, as a structure, a substrate labeled by the labeling substance according to [1] or [2].

[4]
A substrate for measurement suitable for a measurement using an electrochemical measurement method, containing, as a structure, a substrate labeled by the labeling substance according to [1] or [2], and represented by the following general formula (2).

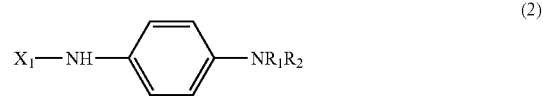

(2)

(In formula (2) above, $X_1$ is a substrate (residue), $R_1$ is H or an alkyl group ($C_mH_{2m+1}$), m is an integer of 1 to 4, $R_2$ is an alkyl group ($C_nH_{2n+1}$), and n is an integer of 1 to 4.)

[5]

A substrate for measurement containing an amide bond, suitable for a measurement using an electrochemical measurement method, wherein the substrate for measurement contains, as a structure, a substrate labeled by the labeling substance according to [1] or [2], and represented by the following general formula (3).

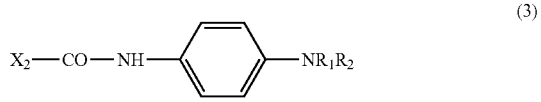

(3)

(In formula (3) above, $X_2$ is a substrate (residue), $R_1$ is H or an alkyl group ($C_mH_{2m+1}$), m is an integer of 1 to 4, $R_2$ is an alkyl group ($C_nH_{2n+1}$), and n is an integer of 1 to 4.)

[6]

The substrate for measurement according to any one of [3] to [5], wherein the substrate is a peptide.

[7]

The substrate for measurement according to [6], wherein the amide bond (—CO—NH—) is a covalent bond formed through reaction of a carboxyl group at the C-terminus of the peptide and an amino group of the labeling substance according to [1] or [2].

[8]

The substrate for measurement according to [6] or [7], wherein the peptide is a peptide having an Arg (R) residue at the C-terminus.

[9]

The substrate for measurement according to any one of [6] to [8], wherein the peptide is a peptide represented by any one of the following general formulas (a) to (g):

Y-Asp-Pro-Arg (Y-DPR)         (a)

Y-Val-Pro-Arg (Y-VPR)         (b)

Y-Leu-Thr-Arg (Y-LTR)         (c)

Y-Met-Thr-Arg (Y-MTR)         (d)

Y-Leu-Gly-Arg (Y-LGR)         (e)

Y-Ile-Glu-Gly-Arg (Y-IEGR)    (f)

Y-Glu-Gly-Arg (Y-EGR)         (g)

(In the formulas (a) to (g) above, Y may be present or may not be present, and when Y is present, Y is a protective group of an amino group of amino acid at the N-terminus of the peptide.)

[10]

The substrate for measurement according to [9], wherein the protective group is Cbz (benzyl oxycarbonyl group) or Boc (tert-butoxycarbonyl group).

[11]

A measurement method using an electrochemical measurement method, using the substrate for measurement according to any one of [3] to [10].

[12]

The measurement method according to [11], wherein the measurement method is a method of measuring a measurement target substance, including the following steps (1) and (2):

(1) a step of bringing the substrate for measurement according to any one of [3] to [10] into contact with an enzyme that degrades the substrate, in the presence of the measurement target substance.

(2) a step of measuring a labeling substance freed from the substrate for measurement used in (1) by an electrochemical measurement method.

[13]

The measurement method according to [12], wherein the measurement target substance is a microbially derived substance.

[14]

The measurement method according to [13], wherein the microbially derived substance is endotoxin and/or (1→3)-β-D-glucan.

[15]

The measurement method according to any one of [12] to [14], wherein the degrading enzyme is a *Limulus* Factor C, B, or G and/or a proclotting enzyme.

[16]

The measurement method according to [11], wherein the measurement method is a method of measuring enzyme activity, including the following steps (1) and (2):

(1) a step of bringing the substrate for measurement according to any one of [3] to [10] into contact with an enzyme that degrades the substrate.

(2) a step of measuring a labeling substance freed from the substrate for measurement used in (1) by an electrochemical measurement method.

[17]

The measurement method according to any one of [11] to [16], wherein the electrochemical measurement method is a voltammetric method or an amperometric method.

[18]

A reagent kit including, as components, the labeling substance according to [1] or [2], and/or the substrate for measurement according to any one of [3] to [10].

Effect of the Invention

According to the present invention, a highly sensitive and stable measurement using an electrochemical measurement method can be performed.

EMBODIMENT OF THE INVENTION

<1> Labeling Substance of the Present Invention

In the present invention, a labeling substance (hereinafter, referred to as "labeling substance of the present invention") to be used to label a substrate to obtain a measuring substrate suitable for a measurement using an electrochemical measurement method, which enables a highly sensitive and stable measurement using the electrochemical measurement method, is provided. The labeling substance of the present invention can be used to prepare, for example, the substrate for measurement of the present invention described below.

The labeling substance of the present invention is a labeling substance (phenylenediamine derivative) containing a structure obtained by modifying one of the amino groups of phenylenediamine ($NH_2$—$C_6H_4$—$NH_2$) by one or two alkyl groups. In other words, the labeling substance of the present invention is a labeling substance containing the structure represented by the general formula (1) shown above. When the labeling substance of the present invention is a phenylenediamine derivative modified by two alkyl groups, the two alkyl groups may respectively have the same structure or may have a different structure.

In the labeling substance of the present invention, the labeling substance containing a structure includes a case where the labeling substance is composed of the structure.

In the present invention, the alkyl group may be a monovalent alkyl group. The alkyl group may be a linear alkyl group that does not have a branched chain.

A chain length of the alkyl group ($C_mH_{2m+1}$, $C_nH_{2n+1}$) is preferably short from the perspective of solubility into an aqueous solvent, and m and n are preferably integers of 1 to 4 (m and n are 1, 2, 3, or 4). In other words, the alkyl group is preferably a methyl group ($CH_3$), an ethyl group ($C_2H_5$), a propyl group ($C_3H_7$), or a butyl group ($C_4H_9$). In the alkyl group ($C_mH_{2m+1}$ and $C_nH_{2n+1}$), m and n are more preferably integers of 1 to 3, still more preferably integers of 1 or 2, and further preferably integers of 1. The ranges or numbers of m and n may be the same range or the same integer, or may be different ranges or different integers.

Specifically, the labeling substance of the present invention is preferably N-methyl-p-phenylenediamine (MPDD) or N, N-dimethyl-p-phenylenediamine (DMPD) represented by the following general formula (4).

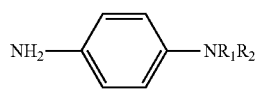

(4)

In formula (4), $R_1$ is H or a methyl group ($CH_3$), and $R_2$ is a methyl group ($CH_3$).

The labeling substance of the present invention is particularly preferably N-methyl-p-phenylenediamine (MPDD) represented by the following general formula (5).

(5)

In formula (5), $R_1$ is H, and $R_2$ is a methyl group ($CH_3$).

The labeling substance of the present invention may be provided as a reagent containing the labeling substance of the present invention. The labeling substance of the present invention and a reagent containing this labeling substance may have any form, and may be, for example, a solid such as powder, or may be a liquid dissolved in any solvent.

According to the labeling substance of the present invention, by using this, a substrate can be labeled to obtain a substrate for measurement suitable for a measurement using an electrochemical measurement method, and a highly sensitive and stable measurement using an electrochemical measurement method can be performed.

<2> Substrate for Measurement of the Present Invention

As described above, the labeling substance of the present invention is a compound to be used to label a substrate to obtain a substrate for measurement suitable for a measurement using an electrochemical measurement method. Preferably, a substrate is labeled by reacting with an amino group of the labeling substance of the present invention and being bonded to the labeling substance, and accordingly, the substrate becomes a substrate for measurement suitable for a measurement using an electrochemical measurement method.

A substrate for measurement containing a substrate labeled by the labeling substance of the present invention as a structure (hereinafter, referred to as "substrate for measurement of the present invention") is preferably a compound represented by the general formula (2) shown above. The substrate for measurement of the present invention can be used to perform an electrochemical measurement method, preferably, a method of measuring the measurement target substance of the present invention and a method of measuring enzyme activity of the present invention described below. The substrate for measurement of the present invention has a property to free the labeling substance of the present invention, for example, when it is coexistent (existent in the same solution) with a measurement target substance under the conditions shown in the measurement method of the measurement target substance of the present invention.

In the substrate for measurement of the present invention, the substrate for measurement containing a substrate labeled by the labeling substance of the present invention as a structure includes a case where the substrate for measurement is composed of a structure of the substrate labeled by the labeling substance of the present invention.

The labeling substance of the present invention is preferably introduced into a substrate via an amino group ($NH_2$ group) of a compound represented by the general formula (1) shown above. Therefore, the substrate preferably has a functional group to be bonded to an amino group. The functional group of the substrate to be bonded to an amino group of the labeling substance of the present invention is not particularly limited as long as it is a functional group that can be bonded to an amino group. Such a functional group includes a carboxyl group, a thiol group, an aldehyde group, and a maleimide group. The functional group may be a functional group introduced into the substrate by a covalent bond to another molecule having the functional group, or may be a functional group that the substrate intrinsically has. Specifically, another molecule mentioned here includes a linker. Another molecule mentioned here may be a low-molecular compound with a molecular weight of 1,000 or less, preferably, 100 or less.

The functional group of the substrate to be bonded to an amino group of the labeling substance of the present invention is preferably a carboxyl group. Therefore, the bond between the labeling substance of the present invention and the substrate is preferably an amide bond. The substrate for measurement of the present invention is preferably a compound having an amide bond and represented by the general formula (3) shown above.

The kind of the substrate is not particularly limited. The substrate includes carbohydrates, sugar, nucleic acids, lipids, proteins, polypeptides, peptides, and amino acids.

In the substrate for measurement of the present invention, the substrate is preferably a peptide. A peptide is, for example, preferably used as a substrate in a measurement using protease. In the substrate for measurement of the present invention, the amide bond is preferably a covalent bond formed by reaction between a carboxyl group at the C-terminus of the peptide (carboxyl group that the peptide intrinsically has at the C-terminus) and the amino group of the labeling substance of the present invention.

The substrate that the substrate for measurement of the present invention has may be one, two, or more kinds. The substrate that the substrate for measurement of the present invention has may be one, two, or more. For example, in the substrate for measurement of the present invention, imide may be formed by bonding carboxyl groups of two peptides to the amino group of the labeling substance of the present invention.

A chain length of the peptide mentioned here is not particularly limited. The peptide preferably has a short chain from the perspective of a yield of a compound to be obtained by labeling reaction using the labeling substance of the present invention (reaction to cause bonding to the labeling substance of the present invention), and is preferably an oligopeptide. Specifically, the peptide preferably has not more than 10 residues. The peptide preferably has not more than 10 residues, not more than 8 residues, not more than 6 residues, not more than 5 residues, or not more than 4 residues. The peptide preferably has 2 or more residues, or 3 or more residues. The peptide preferably has 2 to 10 residues, 2 to 8 residues, 2 to 6 residues, 2 to 5 residues, 2 to 4 residues, 3 to 10 residues, 3 to 8 residues, 3 to 6 residues, 3 to 5 residues, or 3 to 4 residues. The peptide more preferably has 2 to 5 residues, still more preferably has 2 to 4 residues, and particularly preferably has 3 to 4 residues.

The peptide is preferably a peptide having an Arg (R) residue at the C-terminus. A peptide having an Arg (R) residue at the C-terminus is preferably used as a substrate, for example, in a case where a measurement using serine protease is performed. Such a peptide includes Asp-Pro-Arg (DPR), Val-Pro-Arg (VPR), Leu-Thr-Arg (LTR), Met-Thr-Arg (MTR), Leu-Gly-Arg (LGR), Ile-Glu-Gly-Arg (IEGR) (Seq. ID No. 1), and Glu-Gly-Arg (EGR).

The peptide may be a peptide having a protective group at the N-terminus, etc. The peptide may have a protective group in an amino group at the N-terminus, etc., and may have a protective group in a carboxyl group or a thiol group. The peptide may be, for example, a compound represented by the following general formula (6).

Y-X$_p$ (6)

In formula (6) above, X$_p$ is a peptide, Y may be present or may not be present, and when Y is present, Y is a protective group of an amino group of amino acid at the N terminus of the peptide.

In formula (6) above, X$_p$ is preferably Asp-Pro-Arg (DPR), Val-Pro-Arg (VPR), Leu-Thr-Arg (LTR), Met-Thr-Arg (MTR), Leu-Gly-Arg (LGR), Ile-Glu-Gly-Arg (IEGR) (Seq. ID No. 1), or Glu-Gly-Arg (EGR). X$_p$ is particularly preferably Leu-Gly-Arg (LGR).

Specifically, the substrate for measurement of the present invention is preferably a compound represented by the following general formula (7).

(7)

in formula (7) above, Y may be present or may not be present, and when Y is present, Y is a protective group of an amino group of amino acid at the N-terminus of the peptide, and R$_1$ is H or an alkyl group (C$_m$H$_{2m+1}$), m is an integer of 1 to 4, R$_2$ is an alkyl group (C$_n$H$_{2n+1}$), and n is an integer of 1 to 4.

In formulas (6) and (7) above, the protective group Y is preferably present. In formula (6) above, the peptide may be a peptide having a protective group in a carboxyl group or a thiol group. The protective group includes Cbz (benzyloxycarbonyl group), Boc (tert-butoxycarbonyl group), OBzl (benzyl group), Bz (benzoyl group), and Ac (acetyl group). The protective group to protect an amino group is preferably Cbz or Boc, and more preferably Cbz. The protective group Y is preferably Cbz or Boc, and more preferably Cbz. The protective group to protect a carboxyl group or thiol group is preferably OBzl. For example, Asp-Pro-Arg (DPR) may be a peptide (Asp(OBzl)-Pro-Arg (D(OBzl)PR)) in which a carboxyl group of the Asp residue is protected by OBzl. For example, Ile-Glu-Gly-Arg (IEGR) may be a peptide (Ile-Glu(OBzl)-Gly-Arg(IE(OBzl)GR)) in which a carboxyl group of the Glu residue is protected by OBzl. Further, for example, Glu-Gly-Arg (EGR) may be a peptide (Glu(OBzl)-Gly-Arg(E(OBzl)GR)) in which a carboxyl group of the Glu residue is protected by OBzl. In particular, Glu-Gly-Arg (EGR) is preferably Glu(OBzl)-Gly-Arg(E(OBzl)GR).

More specifically, the substrate for measurement of the present invention is preferably a compound represented by the following general formula (8).

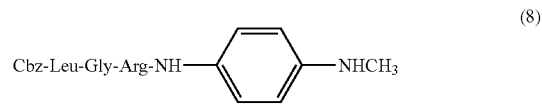

(8)

In formula (8) above, CbZ is a benzyloxycarbonyl group.

In general formulas (2), (3), and (7) above, preferred forms of R$_1$ and R$_2$ can be selected by applying mutatis mutandis the description in the labeling substance of the present invention. For example, in general formulas (2), (3), and (7) above, m and n are preferably 1. Also, for example, in general formulas (2), (3), and (7) above, R$_1$ is preferably H or CH$_3$, and R$_2$ is preferably CH$_3$. In addition, for example, in general formulas (2), (3), and (7) above, R$_1$ is preferably H, and R$_2$ is preferably CH$_3$.

The substrate for measurement of the present invention may be salt. The substrate for measurement of the present invention may be, for example, alkali metal salt, trifluoroacetate (TFA) salt, acetate (AcOH) salt, or hydrochloride (HCl) salt.

The substrate for measurement of the present invention may be provided as a reagent containing the substrate for measurement of the present invention. The substrate for measurement of the present invention and a reagent containing the same may have any form, and may be, for example, a solid such as powder, or may be a liquid dissolved in any solvent.

By using the substrate for measurement of the present invention, a highly sensitive and stable measurement using an electrochemical measurement method can be performed.

<3> Measurement Method of Measurement Target Substance of the Present Invention A measurement method of a measurement target substance of the present invention (hereinafter, referred to as "measurement method 1 of the present invention") is a method of measuring a measurement target substance by an electrochemical measurement method, characterized by using the substrate for measurement of the present invention. Specifically, the measurement method 1 of the present invention is a measurement method of a measurement target substance, including a step of bringing the substrate for measurement of the present invention into contact with an enzyme that degrades the substrate (hereinafter, simply referred to as "degrading enzyme") in the presence of the measurement target substance, and a step of measuring a labeling substance freed from the substrate for measurement.

In the present invention, measurement is used as a generic term including detection, sensing, and quantitative determination. That is, the measurement method 1 of the present invention may be a method of detecting a measurement target substance, a method of sensing a measurement target substance, or a method of determining a quantity of a measurement target substance.

A substance to be measured in the measurement method 1 of the present invention is not particularly limited. The measurement target substance is, for example, a substance that influences activity of a degrading enzyme having activity to free the labeling substance of the present invention by cleaving the substrate for measurement of the present invention. When the substrate for measurement is degraded by the degrading enzyme, the labeling substance of the present invention is freed. The degrading enzyme mentioned here is, for example, protease. That is, by freeing the labeling substance from the substrate for measurement of the present invention containing a peptide, etc., as a substrate, a current value that is obtained when a sample is subjected to an electrochemical measurement method rises, so that activity of the degrading enzyme such as protease can be measured. Further, when a substance to be measured influences activity of a degrading enzyme, a concentration of the substance can be indirectly measured by measuring the activity. A substance that influences activity of a degrading enzyme is, for example, a substance (activator or inhibitor) that acts to enhance or suppress activity of a degrading enzyme. The substance that influences activity of a degrading enzyme is, for example, a substance having a property to convert a degrading enzyme into an activated enzyme by cleaving or the like of a propeptide sequence of a precursor of the degrading enzyme when the substance comes into contact with the precursor. The substance mentioned here is, for example, a microbially derived substance.

The measurement method 1 of the present invention is preferably used as a means to detect microbial contamination by using a microbially derived substance as a measurement target substance. For this purpose, in order to comprehensively measure a level of microbial contamination, it is preferable that a microbially derived substance as a measurement target is an ingredient consisting of an identical structure commonly present in various microbial species. Specifically, the microbially derived substance is preferably endotoxin or (1→3)-β-D-glucan (hereinafter, simply referred to as "glucan").

Endotoxins and glucans can be measured by using, for example, *Limulus* hemocyte extract (*Limulus* amebocyte lysate). The *Limulus* hemocyte extract may be called a *Limulus* reagent or a *Limulus* amebocyte lysate (LAL) reagent, and a test to measure a microbially derived substance by using this extract is called a Limulus test.

Specifically, a Limulus test can be performed by bringing a sample (specimen) containing a microbially derived substance, a *Limulus* reagent, and a substrate for detection for a Limulus test (hereinafter, simply referred to as "substrate for detection") into contact with each other. When a microbially derived substance (specifically, endotoxin or glucan) is present in the specimen, respective factors (Factor C, Factor B, Factor G, proclotting enzyme, which are hereinafter, individually or collectively referred to as "*Limulus* factor") contained in the *Limulus* reagent are successively activated, and accordingly, a cascade reaction progresses.

For example, when endotoxin is present in a specimen, a cascade reaction progresses in which activation of Factor C (production of activated Factor C) by endotoxin, activation of Factor B (production of activated Factor B) by the activated Factor C, and activation of a proclotting enzyme (production of clotting enzyme) by the activated Factor B successively occur. In addition, for example, when glucan is present in a specimen, a cascade reaction progresses in which activation of Factor G (production of activated Factor G) by glucan and activation of a proclotting enzyme (production of clotting enzyme) by the activated Factor G successively occur. Therefore, by measuring an amount of an activated any *Limulus* factor or the progress of a cascade reaction, the measurement target substance of the Limulus test can be measured. Measurement of the progress of a cascade reaction can be performed by, for example, measuring an amount of a clotting enzyme.

For example, the measurement method 1 of the present invention can be performed by using a measuring reagent containing a *Limulus* factor (precursor of a degrading enzyme) of *Limulus*. This measuring reagent is not particularly limited as long as it contains a *Limulus* factor. Such a reagent includes a *Limulus* reagent. The *Limulus* reagent may be acquired in a usual manner by using hemocyte of *Limulus* as a basic ingredient. The *Limulus* reagent may be acquired by properly fractionating and/or purifying, etc., the acquisition.

*Limulus* in the present invention may be any species. *Limulus* includes, for example, *Tachypleus tridentatus* being *Limulus* grown in Asia, *Limulus polyphemus* being *Limulus* grown in America, and *Carcinoscorpius rotundicauda* and *Tachypleus gigas* being limuli grown in South East Asia, and among these, may be any species. *Limulus* is preferably *Tachypleus tridentatus* or *Limulus polyphemus*, and more preferably *Limulus polyphemus*.

The *Limulus* reagent may be, for example, a reagent available on the market. For example, as *Limulus* reagents, Endospecy (SEIKAGAKU CORPORATION), Pyrochrome (ASSOCIATES OF CAPE COD, INC.), Pyrotell-T (ASSOCIATES OF CAPE COD, INC.), Pyrotell Multi-Test (ASSOCIATES OF CAPE COD, INC.), Kinetic-QCL (Lonza Walkersville, Inc.), and Endochrome-K (CHARLES RIVER LABORATORIES, INC.), etc., are available on the market, and can be used in the measurement method 1 of the present invention.

The *Limulus* reagent may be, for example, a *Limulus* reagent artificially reconstituted so as to contain only any *Limulus* factor (hereinafter, referred to as "reconstituted *Limulus* reagent"). The reconstituted *Limulus* reagent is not particularly limited as long as it is constituted to contain a *Limulus* factor that reacts with a measurement target substance of the Limulus test.

For example, when the measurement target substance in the Limulus test is endotoxin, the reconstituted *Limulus* reagent is only required to contain Factor C as a *Limulus* factor, and may contain or may not contain other *Limulus* factors (Factor B, Factor G, and proclotting enzyme). For example, when the measurement target substance in the Limulus test is glucan, the reconstituted *Limulus* reagent is just required to contain Factor G as a *Limulus* factor, and may contain or may not contain other *Limulus* factors (Factor C, Factor B, and proclotting enzyme).

The reconstituted *Limulus* reagent can be prepared through, for example, purification and division to remove any *Limulus* factor from a *Limulus* reagent. For example, one kind of *Limulus* factor isolated from a *Limulus* reagent may be used as the reconstituted *Limulus* reagent, or a mixture of two or more kinds of isolated *Limulus* factors may be used as the reconstituted *Limulus* reagent.

The reconstituted *Limulus* reagent may be prepared by appropriately combining publicly-known methods. The reconstituted *Limulus* reagent can be prepared by referring to, for example, a method described in literature (Nakamura T, Horiuchi T, Morita T, Iwanaga S. J Biochem. 1986 March; 99(3): 847-57).

A *Limulus* factor contained in the reconstituted *Limulus* reagent may be a natural protein obtained from *Limulus*, or a recombinant protein.

A natural *Limulus* factor can be acquired from the *Limulus* hemocyte extract. A recombinant *Limulus* factor can be acquired by expressing a *Limulus* factor in a host cell transformed by using nucleic acid that codes the *Limulus* factor. The kind of the host cell is not particularly limited, however, for example, a mammalian cell or an insect cell can be used. The host cell is preferably a mammalian cell. The mammalian cell includes a Chinese Hamster ovary cell (CHO cell) and a human embryonic kidney cell (HEK cell). The HEK cell includes an HEK 293 cell.

Expression of a recombinant protein using a host cell can be performed in a usual manner. It can be performed by referring to, for example, a method described in Literature (international Publication No. 2012/118226, international Publication No. 2014/092079). An amino acid sequence of a *Limulus* factor and a base sequence of a gene that codes the amino acid sequence can be acquired from a publicly-known database. The publicly-known database includes, for example, NCBT (http://www.ncbi.nlm.nih.gov/). Regarding each expressed recombinant protein, for example, a culture obtained by cultivating a host cell thereof may be directly used as a *Limulus* factor, or the culture purified to a desired extent as necessary may be used as a *Limulus* factor.

All of the *Limulus* factors contained in the reconstituted *Limulus* reagent may be natural proteins, all of the *Limulus* factors may be recombinant proteins, or may be combinations of natural proteins and recombinant proteins as necessary. The reconstituted *Limulus* reagent may be, for example, a *Limulus* reagent itself, or an appropriate combination of a *Limulus* reagent obtained through fractionation and/or purification, etc., and natural and/or recombinant *Limulus* factors.

The substrate for detection is preferably a substrate of a *Limulus* factor to be used to measure an amount of an activated *Limulus* factor and a progress of a cascade reaction. The substrate for detection is not particularly limited as long as it acts as a substrate of a *Limulus* factor. The substrate for detection is preferably the substrate for measurement of the present invention containing a protein, a polypeptide, or a peptide as a substrate. The substrate for detection may be the substrate for measurement of the present invention containing a natural protein or the like as a substrate, or may be the substrate for measurement of the present invention containing a recombinant protein or the like as a substrate. The protein includes coagulogen being a substrate of a clotting enzyme that is an end product of the cascade reaction. For example, natural coagulogen can be prepared from *Limulus* hemocyte extract. For example, recombinant coagulogen can be prepared by referring to a method described in literature (Miyata, et., al., Separate Volume No. 29 of Protein, Nucleic acid, and Enzyme, 1986, P. 30-43).

When the substrate is a polypeptide or peptide, the substrate may be a synthetic substrate chemically synthesized. The synthetic substrate is not particularly limited as long as it is a preferred substrate for measuring an amount of an activated *Limulus* factor or a progress of a cascade reaction. Such a substrate may be a substrate for measuring a clotting enzyme, or may be a substrate for measuring an activated *Limulus* factor present in an intermediate stage of a cascade reaction. The synthetic substrate is preferably a peptide.

The substrate for detection containing the synthetic substrate includes a substrate represented by a general formula of Y-$X_p$-Z (in the formula, Y is a protective group, $X_p$ is a peptide, and Z is a labeled substance (residue) bonded to $X_p$). This synthetic substrate is only required to have a property of freeing the labeled substance Z by cleaving the bond between $X_p$-Z by an activated *Limulus* factor. The bond between $X_p$-Z is preferably an amide bond.

The protective group Y is not particularly limited, and a publicly-known protective substrate applicable to a peptide can be preferably used. Such a protective substrate includes a benzyloxycarbonyl group, a tert-butoxycarbonyl group, a benzyl group, a benzoyl group, and an acetyl group. The peptide $X_p$ includes Asp-Pro-Arg (DPR), Val-Pro-Arg (VPR), Leu-Thr-Arg (LTR), Met-Thr-Arg (MTR), Leu-Gly-Arg (LGR), ile-Glu-Gly-Arg (IEGR) (Seq. ID No. 1), and Glu-Gly-Arg (EGR). As the labeled substance Z, any compound in the labeling substance of the present invention can be used.

As the synthetic substrate, a preferred one can be selected and used as necessary according to a kind of a *Limulus* factor to be detected. For example, as the peptide $X_p$, from the perspective of substrate specificity, a substrate containing LGR or IEGR can be preferably used for a measurement of clotting enzyme, a substrate containing LTR or MTR can be preferably used for a measurement of activated Factor B, a substrate containing VPR or DPR can be preferably used for a measurement of activated Factor C, and a substrate containing EGR can be preferably used for a measurement of activated Factor G.

In a Limulus test using a reconstituted *Limulus* reagent, when two or more kinds of *Limulus* factors are used, each of the *Limulus* factors may be contained in a reaction liquid from the beginning of the step of being brought into contact with a specimen, or may be successively added into the reaction liquid.

The substrate for detection may be added in a reaction liquid in any order. For example, the substrate for detection may be contained in the reaction liquid before the step of bringing the specimen into contact with a *Limulus* reagent, or may be added in the reaction liquid in or after the step. When a *Limulus* reagent containing the substrate for detection in advance is used, the substrate for detection may not be separately added into the reaction liquid.

The electrochemical measurement method in the present invention may be any method. The electrochemical measurement method includes a voltammetric method and an amperometric method. The electrochemical measurement method is preferably an amperometric method. The electrochemical measurement method can be performed by referring to, for example, a method described in literature (Japanese Published Unexamined Patent Application No. 2015-187607).

The measurement method 1 of the present invention may include any other steps. For example, the measurement method 1 of the present invention may include a step of adding a substrate for detection into a reaction liquid as described above. The measurement method 1 of the present invention may, for example, include a step of adding a *Limulus* reagent into a reaction liquid. The measurement method 1 of the present invention may be, for example, a method of measuring a measurement target substance including a step of bringing a substrate for detection being the substrate for measurement of the present invention, a measurement target substance, and a *Limulus* reagent into contact with each other, and a step of measuring a labeling substance freed from the substrate for measurement by an electrochemical measurement method.

Further, for example, the measurement method 1 of the present invention may include a step of converting data obtained through a measurement into other data. The step of converting data obtained through a measurement into other data includes, for example, a step of calculating an amount of a measurement target substance based on data obtained through a measurement. Specifically, such a step is a step of converting a measurement value obtained when measuring a specimen into an amount of a measurement target substance based on a relationship (standard curve) between a measurement value obtained when the specimen is replaced by a standard substance with a known concentration and measured, and the concentration of the standard substance.

In the measurement method 1 of the present invention, reaction is preferably caused in water or an aqueous solvent such as a buffer solution.

By performing the measurement method 1 of the present invention, a measurement target substance can be highly sensitively and stably measured.

<4> Measurement Method of Enzyme Activity of the Present Invention

A measurement method of enzyme activity of the present invention (hereinafter, referred to as "measurement method 2 of the present invention") is a method of measuring activity of a degrading enzyme by an electrochemical measurement method, characterized by using the substrate for measurement of the present invention. The measurement method 2 of the present invention is, for example, a measurement method of enzyme activity including a step of bringing the substrate for measurement of the present invention into contact with a degrading enzyme, and a step of measuring a labeling substance freed from the substrate for measurement. The measurement method 2 of the present invention may include any other steps as in the case of the measurement method 1 of the present invention. Other steps are, for example, a step of converting data (measurement value) obtained through a measurement into an amount of a degrading enzyme based on a standard curve. The description of the measurement method of a measurement target substance of the present invention given in <3> above can be applied mutatis mutandis to describe a degrading enzyme and each step, etc., in the measurement method 2 of the present invention.

<5> Reagent Kit of the Present Invention

A reagent kit of the present invention is a reagent kit including the labeling substance of the present invention and/or the substrate for measurement of the present invention as components. The reagent kit of the present invention can be used to, for example, prepare the substrate for measurement of the present invention and/or perform the measurement method 1 of the present invention or the measurement method 2 of the present invention.

The reagent kit of the present invention may further include other components as long as it includes the labeling substance of the present invention and/or the substrate for measurement of the present invention as a component. Other components mentioned here include, for example, a condensation agent, a *Limulus* reagent, a buffer solution, distilled water, a standard substance (protease standard product, microbially derived substance such as endotoxins and glucans, etc.), a microplate, and a package insert describing product information.

Each *Limulus* factor contained in the *Limulus* reagent and the substrate for measurement of the present invention may be contained as a mixture in the reagent kit of the present invention, or may be contained separately or in arbitrary combinations separately in the reagent kit of the present invention.

By using this reagent kit of the present invention, preparation of the substrate for measurement of the present invention and a measurement using an electrochemical measurement method can be easily performed.

EXAMPLES

Hereinafter, the present invention is described in detail based on examples, however, a technical scope of the present invention is not limited to only these examples.

<Reference Example 1> Acquisition of Labeling Substance and Substrate for Measurement P-aminophenol (pAP), N, N-dimethyl-p-phenylenediamine (DMPD), and N-methyl-p-phenylenediamine (MPDD) being labeling substances were purchased from Wako Pure Chemical Corporation. Cbz-LGR-pAP, Cbz-LGR-DMPD, and Cbz-LGR-MPDD being substrates for measurement obtained by amide-bonding the labeling substances and Cbz-Leu-Gly-Arg (Cbz-LGR) were acquired by contracting out synthesis to WATANABE CHEMICAL INDUSTRIES, LTD. In the examples of the application concerned, a substrate for measurement prepared as TFA (trifluoroacetate) salt was used.

Hereinafter, Cbz-LGR-pAP, Cbz-LGR-DMPD, and Cbz-LGR-MPDD are respectively abbreviated to LGR-pAP, LGR-DMPD, and LGR-MPDD.

<Reference Example 2> Evaluation of Quantitative Performance

As a result of performing a cyclic voltammetric measurement in which the mixture ratio of a substrate and free molecule (labeling substance) was varied in stages, in a voltammogram of a mixed solution of LGR-pAP and pAP, two oxidation peaks at 0.15 V and 0.49 V were confirmed. From individual voltammograms of a substrate molecule and a free molecule, the peak near 0.49 V is considered to be derived from oxidation of LGR-pAP, and the peak near 0.15 V is considered to be derived from oxidation of pAP. Similarly, from a voltammogram of a mixed solution of LGR-DMPD and DMPD, an oxidation peak derived from LGR-DMPD was confirmed near 0.45V, and an oxidation peak derived from DMPD was confirmed near 0.19 V. Further, from a voltammogram of a mixed solution of LGR-MPDD and MPDD, an oxidation peak derived from LGR-MPDD was confirmed near 0.46 V, and an oxidation peak derived from MPDD was confirmed near 0.14 V. Further, when using any substrate, an oxidation peak current value of free molecules increased as the percentage of a free molecule increased. From these facts, it was considered that a concentration of free molecules in each mixed solution could be amperometrically quantified at a potential of 0.3 V vs. Ag/AgCl. Next, in each mixed solution, chronoamperometry was performed. Based on a temporal change in current value just after (0 seconds) a potential of a working electrode was changed to 0.3 V vs. Ag/AgCl, a current value at 20 seconds with respect to a concentration of a free molecule in each mixed solution was plotted, and as a result, determination coefficients were $R_2=0.9973$ for pAP, $R_2=0.9986$ for DMPD, and $R_2=0.9972$ for MPDD, and high linearity was confirmed.

<Example 1> Evaluation of Stability of Labeling Substances and Substrates for Measurement Stabilities of compounds of the labeling substances and substrates for measurement acquired in <Reference Example 1> were evaluated.

The labeling substances (pAP, MPDD, and DMPD) and the substrates for measurement (LGR-pAP, LGR-MPDD, LGR-DMPD) were dissolved into 0.1 M HEPES (pH 7.8) and prepared to be 1 mM, and were left to stand for 1 to 24 hours in an incubator at 37° C. Thereafter, a test was performed according to the following procedures.

<Electrochemical Measurement Method>

As an electrochemical measurement method, cyclic voltammetry and a potential step chronoamperometric method were used. As a measuring device, a working electrode, a reference electrode, and a counter electrode, those described in <Measurement Conditions> below were used. In each measurement, the working electrode, the reference electrode, and the counter electrode were inserted in a solution, and respectively connected to connectors of a potentiostat for a working electrode, a reference electrode, and a counter electrode. After each measurement, the electrode surface of the working electrode was polished with 0.05 m polishing alumina, and cleaned with ultrapure water. In the cyclic voltammetric measurement, potential scanning was performed by setting an initial potential and a finish potential to 0 V, a first turnover potential to 0.4 V (0.6 V for LGR-pAP and LGR-DMPD, 0.7 V for LGR-MPDD), and a second turnover potential to −0.2 V, and the current was monitored. In the potential step chronoamperometric measurement, after 0.0 V was applied to the working electrode for 10 seconds, the potential was momentarily changed to 0.3 V, and the current was monitored for 35 seconds.

<Measurement Conditions>

Measuring device: Potentiostat (CompactStat manufactured by IVIUM)

Working electrode: Glassy carbon disk electrode, 1 mm in diameter (manufactured by BAS)

Reference electrode: Silver-silver chloride electrode

Counter electrode: Platinum electrode

<Confirmation on Stabilities of Substrates and Free Molecules>

50 ml of test solutions (1.0 mM) of the respective substrates (LGR-pAP, LGR-MPDD, LGR-DMPD) and free molecules (pAP, MPDD, DMPD) were prepared by using 0.1 M HEPES (pH=7.8), put in a disposable 50 ml centrifuge tube (manufactured by IWAKI), and left to stand at 37° C. under light-shielded conditions. When a predetermined time (0.5 h, 1 h, 2 h, 4 h, and 24 h) elapsed, 5 ml was sampled from the test solution and subjected to cyclic voltammetric measurement. MPDD was measured when 6 hours and 8 hours elapsed as well. By using a test solution just after preparation, a measurement at a predetermined time of 0 hours was performed.

<Quantitative Evaluation of Free Molecules>

A 1.0 mM LGR-pAP solution and a 1.0 mM pAP solution were prepared by using 0.1M HEPES (pH=7.8), and these were mixed at a ratio of 100:0, 75:25, 50:50, 25:75, or 0:100 to prepare mixed solutions whose pAP concentrations were varied in stages. Mixed solutions of the LGR-DMPD solution and the DMPD solution and mixed solutions of the LGR-MPDD solution and the MPDD solution were also prepared in a similar manner. These mixed solutions were subjected to a cyclic voltammetric measurement.

As a result of the cyclic voltammetric measurements of each synthetic substrate and each free molecule left to stand at 37° C. under light-shielded conditions, from the results of the measurements of the synthetic substrates, it was found that the forms of voltammograms of the synthetic substrates did not greatly change in 24 hours, and were stable. It is considered that in a reaction time of 1 hour in actual endotoxin detection, the synthetic substrates do not deteriorate. On the other hand, from the results of the measurements of the free molecules, it was found that the forms of voltammograms of the free molecules gradually changed in 24 hours, and were lower in stability than the synthetic substrates. These results are shown in Table 1.

TABLE 1

| Time | pAP | DMPD | MPDD |
|------|-----|------|------|
| 0 | 100.0 | 100.0 | 100.0 |
| 0.5 | 94.2 | 95.3 | 102.4 |
| 1 | 95.0 | 94.3 | 102.3 |
| 2 | 83.0 | 84.5 | 101.0 |

The numerical values shown in Table 1 are relative values of heights of peaks in the voltammograms of the free molecules after predetermined times elapse, where the oxidation peak current value just after preparation (0 hours) is set as 100%, in voltammograms of the respective free molecules. Because detection of an endotoxin is usually finished in 1 hour, the oxidation peak current values in voltammograms of pAP, DMPD, and MPDD in one hour after preparation were compared with values just after solution preparation as references, resulting in 95.0%, 94.3%, and 102.3%, respectively.

As shown in Table 1, among the labeling substances that are substances to be freed from the substrate for measurement by *Limulus* reaction, detected values of pAP and DMPD showed a tendency to successively decrease in 2 hours after preparation. However, no decrease in detected value of MPDD was found in 2 hours after preparation.

It was shown above that MPDD is more stable than pAP, and is accordingly a labeling substance that enables a stable measurement.

<Example 2> Limulus Test (1)

Limulus tests using the substrate for measurement acquired in <Reference Example 1> described above were performed, and endotoxin measurements were performed by an amperometric method. As a *Limulus* reagent, Endospecy ES-24S (manufactured by SEIKAGAKU CORPORATION) was used. In the procedures described hereinafter, Endospecy ES-24S is abbreviated to ES-24S. The procedures of the test are described below.

<*Limulus* Reaction>

According to a method prescribed in Japanese Pharmacopoeia, a standard endotoxin sample (USP-RSE) was dissolved into an injection solvent (manufactured by Otsuka Pharmaceutical Co., Ltd.) to prepare endotoxin solutions of 20,000 EU/L, 2,000 EU/L, 200 EU/L, 20 EU/L, 2 EU/L, and 0 EU/L. In addition, a 1.0 mM LGR-pAP solution was prepared by using a buffer solution supplied with ES-24S, and by using this solution, the *Limulus* reagent ES-24S was dissolved. Each endotoxin solution at the respective concentration and the *Limulus* reagent containing LGR-pAP were mixed at a volume ratio of 1:1 and reacted for 1 hour at 37° C., and thereafter, subjected to a chronoamperometric measurement. For LGR-DMPD and LGR-MPDD, the tests were also performed using the same procedures. The solution of 20,000 EU/L was measured only once, and for the solutions of 2,000 EU/L, 200 EU/L, 20 EU/L, 2 EU/L, and 0 EU/L, the test from the solution preparation to the measurement was performed for three times on different measurement dates.

<Measurement Conditions>

The conditions are the same as those described in <Measurement Conditions> of <Example 1> described above.

The results are shown in Table 2.

TABLE 2

| EU/L | LGR-pAP | LGR-DMPD | LGR-MPDD |
|---|---|---|---|
| 0 | 0.023 ± 0.005 | 0.008 ± 0.001 | 0.010 ± 0.000 |
| 1 | 0.033 ± 0.011 | 0.015 ± 0.002 | 0.012 ± 0.001 |
| 10 | 0.075 ± 0.032 | 0.021 ± 0.002 | 0.022 ± 0.002 |
| 50 | 0.275 ± 0.006 | 0.039 ± 0.013 | 0.061 ± 0.001 |
| 100 | 0.313 ± 0.027 | 0.075 ± 0.011 | 0.087 ± 0.007 |
| 1,000 | 0.276 ± 0.013 | 0.130 ± 0.013 | 0.235 ± 0.003 |

The numerical values shown in Table 2 are averages of measured values (current values/PA after 20 seconds in amperograms) and standard deviations obtained when the Limulus test was performed 3 times by using the respective substrates. In the present example, measurable ranges of endotoxin concentration when using each substrate were evaluated by using a value calculated by adding a value three times the standard deviation to an average of the measured values of the sample of 0 EU/L as a detection limit value.

From Table 2, when a conventional substrate for measurement (LGR-pAP) is used, a measured value of the sample of 1 EU/L was not more than the detection limit value. In addition, a measured value of the sample of 100 EU/L was higher than a measured value of the sample of 1,000 EU/L. That is, it was shown that when the conventional substrate for measurement (LGR-pAP) was used, a quantitative range of endotoxin concentration was 1.0 to 100 EU/L.

On the other hand, when the substrate for measurement (LGR-MPDD, LGR-DMPD) of the present invention was used, a measured value of the sample of 1 EU/L exceeded the detection limit value, and the measured value increased in proportion to an endotoxin concentration in an endotoxin concentration range of 1 to 1,000 EU/L. That is, it was shown that when the substrate for measurement (LGR-MPDD, LGR-DMPD) of the present invention was used, a quantitative range of endotoxin concentration was 1 to 1,000 EU/L, and this shows that a wider range of endotoxin concentration can be quantified as compared with a case where a conventional substrate for measurement (LGR-pAP) is used.

Values of standard deviations when measurements were performed by using the substrates for measurement (LGR-MPDD, LGR-DMPD) of the present invention were found to become smaller than a value of a standard deviation when a measurement was made by using a conventional substrate for measurement (LGR-pAP). That is, it was shown that, by using MPDD or DMPD as a labeling molecule, stable measurements with reduced daily errors were enabled. Further, it was found that, when measurements were performed by using the substrates for measurement (LGR-MPDD, LGR-DMPD) of the present invention, measured values of the sample of 0 EU/L were smaller than in the case where a measurement was performed by using LGR-pAP, showing the background of the measured value can be kept low.

<Example 3> Limulus Test (2)

Limulus tests using the substrates for measurement acquired in <Reference Example 1> described above were performed, and measurements of endotoxin were performed by a voltammetric method. The test procedures are shown below.

<*Limulus* Reaction>

The same conditions as those described in <*Limulus* Reaction> of <Example 2> described above were applied except that a cyclic voltammetric measurement was performed instead of the chronoamperometric measurement.

<Measurement Conditions>

The same conditions as described in <Measurement Conditions> of <Example 1> above were applied.

As a result of measurements according to a voltammetric method, when using any of LGR-pAP, LGR-DMPD, and LGR-MPDD as a substrate, only an oxidation peak of the substrate was observed in the absence of endotoxin (0 EU/L). On the other hand, it was confirmed that in the presence of endotoxin, as the endotoxin concentration increase, an oxidation peak derived from a free molecule became higher. When using a conventional substrate for measurement (LGR-pAP) as a substrate, an oxidation peak derived from a free molecule when the sample of 1,000 EU/L was set as a measurement target was smaller than that in the case where the sample of 100 EU/L was set as a measurement target. On the other hand, when the substrate for measurement (LGR-MPDD, LGR-DMPD) of the present invention was used, in the endotoxin concentration range of 1 to 1,000 EU/L, an oxidation peak derived from a free molecule increased in proportion to the endotoxin concentration. That is, it was shown that the endotoxin concentration could be measured in the case using a voltammetric method as an electrochemical measurement method in a similar manner as in the case using an amperometric method.

In a voltammogram at this time, a current value of an oxidation peak derived from a free molecule in the case where the sample of 1,000 EU/L was set as a measurement target was 0.31 µA when LGR-DMPD was used as a substrate, and 0.60 µA when LGR-MPDD was used as a substrate. On the other hand, a voltammogram of LGR-pMA being a substrate labeled by para methoxyaniline (pMA), is disclosed in FIG. 9 of Patent Literature 1, and a current value of an oxidation peak caused by a free molecule when the sample of 1,000 EU/L is set as a measurement target is approximately 0.3 µA. That is, it was shown that by using the labeling substance (MPDD or DMPD) of the present invention, a current value equal to or higher than that in the case where the conventional labeling substance (pMA) was used was obtained. In particular, it was clarified that when using MPDD as a labeling substance, a current value was obtained approximately twice as high as a current value when pMA was used, and this shows that a highly sensitive measurement of endotoxin can be available.

Oxidation peak current values caused by 0.5 mM DMPD and MPDD, shown by the results shown in <Reference Example 2>, were approximately 0.9 µA and approximately 1.1 µA, respectively. On the other hand, FIG. 4 of Patent Literature 1 shows that an oxidation peak current value caused by 1 mM pMA is approximately 3.0 µA, so that an oxidation peak current value caused by 0.5 mM pMA is approximately 1.5 µA. That is, from the results of measurement of a free molecule itself, both of MPDD and DMPD being labeling substances to be used for preparation of the substrate for measurement of the present invention were presumed to show lower current values as compared with that of pMA being a conventional labeling substance. However, although FIG. 8 of Patent Literature 1 shows that a maximum value (upper limit) of an oxidation peak current value obtained when bonded to the substrate (LGR) and used for a Limulus test is approximately 0.28 µA when using LGR-pMA, maximum values when using LGR-DMPD and LGR-MPDD being the substrates for measurement of the present invention were 0.31 µA and 0.60 µA. These values are shown in Table 3.

method can be performed. Therefore, the present invention is extremely useful in both clinical practice and research practice.

The disclosure of Japanese Patent Application No. 2016-026925 (date of filing: Feb. 16, 2016) is incorporated herein by reference in its entirety. All literatures, patent applications, and technical standards described herein are incorporated herein by reference to the same extent as if individual literatures, patent applications, and technical standards are specifically and individually indicated to be incorporated by reference.

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Ile Glu Gly Arg
1
```

TABLE 3

| Labeling reagent | Measured value A | Measured value B | Measured value B/ Measured value A (%) |
| --- | --- | --- | --- |
| MPDD | 1.1 µA | 0.60 µA | 55% |
| DMPD | 0.9 µA | 0.31 µA | 34% |
| pMA | 1.5 µA | 0.28 µA | 19% |

In Table 3, the measured value A shows an oxidation peak current value when each of 0.5 mM labeling substances itself is measured by a voltammetric method, and the measured value B shows a maximum value of an oxidation peak current value obtained by using, for a Limulus test, a substrate for measurement (0.5 mM) obtained by bonding each labeling substance to a peptide (LGR).

That is, when using any of the labeling substances, a maximum value (upper limit) of an oxidation peak current value obtained after the labeling substance was bonded to the peptide and used for a Limulus test showed a tendency to be lower than an oxidation peak current value estimated from a molarity, however, when using MPDD and DMPD being the labeling substances of the present invention, the degree of decrease was reduced as compared with the case using pMA being a conventional labeling substance, and these were found to be efficiently sensed in an electrochemical measurement method. Based on a measured value of a labeling substance alone, while a person skilled in the art expects that pMA is more efficiently sensed in an electrochemical measurement method when used as a substrate for measurement, the result that MPDD and DMPD are more efficiently sensed is unexpected. This result is particularly noticeable in MPDD.

INDUSTRIAL APPLICABILITY

According to the present invention, a highly sensitive and stable measurement using an electrochemical measurement

The invention claimed is:

1. A method of measuring an endotoxin and/or (1→3)-β-D-glucan in a sample, comprising:
   (1) contacting the sample with a measuring substrate represented by formula (2):

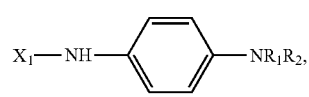

(2)

wherein $R_1$ is H, $R_2$ is methyl, and $X_1$ is a peptide with an Arg (R) residue at the C-terminus which is coupled to the NH group of the measuring substrate by an amide bond and an enzyme that degrades the measuring substrate when the endotoxin and/or (1→3)-β-D-glucan is present in the sample, and
   (2) measuring the cleavage of the peptide from the measuring substrate by the enzyme by an electrochemical measurement method.

2. The method according to claim 1, wherein the enzyme is a *Limulus* Factor C, B, or G and/or a pro-clotting enzyme.

3. The method according to claim 1, wherein the electrochemical measurement method is a voltammetric method or an amperometric method.

4. The method according to claim 1, wherein the peptide having the Arg group at the C-terminus is a peptide represented by any one of the following formulas (a) to (g):

| | |
| --- | --- |
| Y-Asp-Pro-Arg (Y-DPR) | (a), |
| Y-Val-Pro-Arg (Y-VPR) | (b), |
| Y-Leu-Thr-Arg (Y-LTR) | (c), |
| Y-Met-Thr-Arg (Y-MTR) | (d), |

Y-Leu-Gly-Arg (Y-LGR)                         (e),

Y-Ile-Glu-Gly-Arg (Y-IEGR) (SEQ ID No. 1)     (f), and

Y-Glu-Gly-Arg (Y-EGR)                         (g);

wherein Y may be present or may not be present, and when Y is present, Y is a protective group of an amino group of amino acid at the N-terminus of the peptide.

5. The method according to claim 4, wherein the protective group is Cbz (benzyl oxycarbonyl group) or Boc (tert-butoxycarbonyl group).

* * * * *

UNITED STATES PATENT AND TRADEMARK OFFICE
CERTIFICATE OF CORRECTION

PATENT NO. : 10,883,963 B2
APPLICATION NO. : 16/076614
DATED : January 5, 2021
INVENTOR(S) : Hikaru Mizumura et al.

It is certified that error appears in the above-identified patent and that said Letters Patent is hereby corrected as shown below:

On the Title Page

Item (56) References Cited, Other Publications, at page 2, Line 6, "PCT/JP2017/00514" should read "PCT/JP2017/005514"

In the Specification

Column 7, Line 53, "in formula" should read "In formula"

Column 10, Line 55, "Factor Gas" should read "Factor G as"

Column 11, Line 26, "NCBT" should read "NCBI"

Column 12, Line 19, "ile-Glu-Gly-Arg" should read "Ile-Glu-Gly-Arg"

Column 15, Line 28, "0.05 m" should read "0.05 μm"

Column 17, Line 25, "values/PA" should read "values/μA"

Column 17, Line 41, "1.0" should read "10"

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*